US012740700B2

(12) United States Patent
Wojdas

(10) Patent No.: US 12,740,700 B2
(45) Date of Patent: Sep. 22, 2026

(54) METHOD, A DEVICE AND A SYSTEM FOR NUMERICAL DATA PROCESSING

(71) Applicant: OPTOPOL Technology Spolka z ograniczona odpowiedzialnoscia, Zawiercie (PL)

(72) Inventor: Lukasz Wojdas, Zawiercie (PL)

(73) Assignee: OPTOPOL TECHNOLOGY SPOLKA Z OGRANICZONA ODPOWIEDZIALNOSCIA, Zawiercie (PL)

( * ) Notice: Subject to any disclaimer, the term of this patent is extended or adjusted under 35 U.S.C. 154(b) by 81 days.

(21) Appl. No.: 19/045,079

(22) Filed: Feb. 4, 2025

(65) Prior Publication Data

US 2025/0248594 A1 Aug. 7, 2025

(30) Foreign Application Priority Data

Feb. 6, 2024 (EP) .................................... 24461523

(51) Int. Cl.
*A61B 3/10* (2006.01)
*G01B 9/02055* (2022.01)

(52) U.S. Cl.
CPC .......... *A61B 3/102* (2013.01); *G01B 9/02072* (2013.04)

(58) Field of Classification Search
CPC ................ A61B 3/102; G01B 9/02072; G01B 9/02089; G01B 9/02091

(Continued)

(56) References Cited

U.S. PATENT DOCUMENTS

2017/0290514 A1 10/2017 Liu et al.
2019/0343390 A1* 11/2019 Boppart ................ A61B 1/227
2023/0172448 A1 6/2023 Yang et al.

FOREIGN PATENT DOCUMENTS

WO 2011/091369 7/2011

OTHER PUBLICATIONS

Vergnole, S. et al., "Experimental validation of an optimized signal processing method to handle non-linearity in swept-source optical coherence tomography", Optics Express, vol. 18, No. 10, May 2010, pp. 10446-10461.

(Continued)

*Primary Examiner* — MD M Rahman
(74) *Attorney, Agent, or Firm* — Wenderoth, Lind & Ponack, L.L.P.

(57) ABSTRACT

The object of the invention is a system, a device and a method for numerical processing of input data, which input data have the form of N measurement results forming a vector with coordinates numbered from 0 to N−1, and which input data have been recorded in a detector, in an optical coherence tomography device, OCT, during a process involving:

- the emission of light by a light source,
- splitting the light in a coupler into at least two paths, meaning: a reference path, in which a reference light beam is reflected from a mirror, and a sample path, in which a sample light beam is reflected from the object under examination,
- reflecting said reference light beam in at least one reference path from the mirror and
- reflecting said sample light beam in at least one sample path from the object under examination,
- mutual merging and interference of the reference light beam and the sample light beam in the coupler, (Continued)

recording the data in the form of a spectrum of merged light beams within a specified light wavelength range by means of said detector as said vector of N measurement results.

13 Claims, 7 Drawing Sheets

(58) Field of Classification Search
USPC .......................................................... 356/456
See application file for complete search history.

(56) References Cited

OTHER PUBLICATIONS

Attendu, X. et al., “Simple and robust calibration procedure for k-linearization and dispersion compensation in optical coherence tomography”, Journal of Biomedical Optics, vol. 24, Issue 5, May 2019, pp. 056001-1-056001-11.

* cited by examiner

METHOD, A DEVICE AND A SYSTEM FOR NUMERICAL DATA PROCESSING

TECHNICAL FIELD

The object of the invention is a method for numerical processing of data acquired by means of the OCT method (optical coherence tomography) and a device used for OCT imaging (optical coherence tomography). A change in the height of the imaging window in accordance with this method takes place without interfering with its optical system.

PRIOR ART

Methods for processing data from OCT devices are known from prior art. Their principle is based on the emission of light by a light source, which is subsequently split in a coupler into two paths, the first being a reference one, and the second being a sample one. After reflecting in these paths, it returns along the same way, and it merges and interferes with itself in the coupler. Subsequently, it reaches a detector, where the spectrum of this light is recorded.

According to the solutions known from prior art, measurement data from an OCT device are converted from a wavelength domain to a wavenumber domain, so that the distances of specific wavenumbers on specific photosensitive elements of the detector are placed at an equal distance from each other. It seems natural to use virtually the entire recorded signal from a single measurement, that is to collect a single set of N measurements and assign it to the whole length of the photosensitive element of the detector, resulting in a specific imaging window and resolution.

The document WO2011091369A1 describes a device using the method of changing the imaging window, including in SD-OCT devices (spectral domain optical coherence tomography) in order to examine biological samples. This patent describes a numerical method in which two or more sets of measurements are performed. A processor is used to recalculate two or more imaging windows with different Gaussian spectral widths. Different windows are used in order to simultaneously reach high spectral resolution and a wide depth range of the structures which are being imaged. The first one of the windows is narrower, thus providing higher spectral resolution of the device. The second window is in turn wider, which allows for the imaging of a wider depth range compared to the first window. These windows are separated in time, and they have different central wavelengths. The imaging is performed for both windows, and subsequently a single image is put together from them, characterised by both abovementioned features. The resulting image, which is a combination of several windows with different spectral widths, has high axial resolution and high spectral resolution. A negative aspect of this solution is the necessity to perform at least two measurements of the sample under examination in order to acquire a single image with a wider depth range compared to a single measurement. For example, the user cannot use the data collected on the previous day in order to change the height of the imaging window without taking further sets of measurements. In addition, when working with biological tissue, for example a human eye, two consecutive measurements may differ from each other due to the person's movement, causing noises visible in the image.

The document US20230172448A1 describes systems and methods for performing optical coherence tomography angiography for the rapid generation of en face images. Differential interferograms generated using a spectral domain or a swept source optical coherence tomography system are convolved with a Gabor filter, where the Gabor filter is computed according to an estimated depth of the tissue surface. A Gabor-convolved differential interferogram. The method according to the invention allows for the rapid generation of en face images by combining a plurality of depth images. The interferogram is processed to produce an en face image, without requiring the performance of a Fourier transform and k-space resampling for the individual depth images. The solution additionally describes using only some of the pixels for accelerating the throughput and the image generation process, minimising the data necessary for the generation of a sharp image.

The document US20170290514A1 describes a method for increasing axial resolution in optical coherence tomography (OCT) to cellular and subcellular levels. The method comprises: generating a k-space interferogram of an OCT spectral image; uniform transformation of the k-space interferogram into a quasi-stationary interferogram by separating a source envelope; adjusting the spectral estimation model to the quasi-stationary interferogram; and calculating an axial depth profile using the adjusted spectral estimation model. The resolution is increased by combining measurements from a plurality of spectral bands into a single combined spectrum (FIG. 11), followed by the filling of the gaps between the signals of discontinuous spectra. A drawback of this solution is the necessity to perform several measurements to improve the image resolution.

The publication "*Experimental validation of an optimized signal processing method to handle non-linearity in swept-source optical coherence tomography*" by S. Vergnole, D. Levesque and G. Lamouche describes various signal processing methods evaluated to address the non-linearity in wavenumber space commonly found in swept-source optical coherence tomography. The methods compared using the same experimental data include non-uniform discrete Fourier transforms with a Vandermonde matrix or Lomb periodogram, resampling with linear interpolation or spline interpolation before performing a fast Fourier transform (FFT), and resampling with convolution before FFT. This method requires a minimal fractional oversampling factor between 1 and 2, resulting in reduced computational time while maintaining high image quality.

SUMMARY OF INVENTION

The purpose of the invention is to provide a method for arbitrary and multiple conversions of input data collected from an OCT device into output data by means of properly selected calibration parameters. This allows for changing the imaging window and the image resolution on the basis of the data collected during a single measurement without changes in the optical system. The device according to the invention has increased reliability due to a smaller number of optical and mechanical elements. In addition, changing the imaging window and changing the resolution require very low processing power.

The object of the invention is a computer-implemented method for numerical processing of input data, which input data have the form of N measurement results forming a vector with coordinates numbered from 0 to N−1. The input data have been recorded in a detector in an optical coherence tomography device, OCT, during a process involving:

the emission of light by a light source;

splitting the light in a coupler into at least two paths, meaning:

at least one reference path 4, in which a reference light beam is reflected from a mirror;

at least one sample path 5, in which a sample light beam is reflected from the object under examination;

reflecting said reference light beam in at least one reference path 4 from the mirror;

reflecting said sample light beam in at least one sample path 5 from the object under examination;

mutual merging and interference of the reference light beam and the sample light beam in the coupler;

optional passing of the merged light beams across a diffraction grating;

recording the data in the form of a spectrum of merged light beams within a specified light wavelength range by means of said detector as said vector of N measurement results.

k-space resampling a first subset of input data, i.e. the input data saved in said vector of N measurement results as coordinates numbered from $n1_{in\_min}$ to $n1_{in\_max}$, where $0 \le n1_{in\_min} < n1_{in\_max} \le N-1$, wherein the k-space resampling is described by means of a first set of calibration parameters, into a first subset of output data, in which first subset of output data, the values of the output data, meaning the data after k-space resampling, are saved in the form of a first vector of output data, with coordinates numbered from $n1_{out\_min}$ to $n1_{out\_max}$.

The method is characterised in that it comprises the step of at the user's request, k-space resampling a second subset of input data, i.e. the input data saved in said vector of N measurement results as coordinates numbered from $n2_{in\_min}$ to $n2_{in\_max}$, where $0 \le n2_{in\_min} < n2_{in\_max} \le N-1$, wherein the k-space resampling is described by means of a second set of calibration parameters, into a second subset of output data, in which second subset of output data, the values of the output data, meaning the data after k-space resampling, are saved in the form of a second vector of output data, with coordinates numbered from $n2_{out\_min}$ to $n2_{out\_max}$. The first subset of input data differs in at least one element from the second subset of input data, and/or the first set of calibration parameters differs in at least one parameter from the second set of calibration parameters, wherein the first output data (11) resampled by means of the first calibration parameters has a greater or narrower spectral width of wavelength in comparison to the second output data (11) resampled by means of the second calibration parameters.

Preferably, a first tomogram with a first resolution and a first height of the imaging window is generated on the basis of the first subset of output data. Additionally, at the user's request, a second tomogram with a second resolution and a second height of the imaging window is generated on the basis of the second subset of output data.

Preferably, the first resolution is different from the second resolution, and/or the first height of the imaging window is different from the second height of the imaging window.

Preferably, prior to the k-space resampling of the first subset of input data and optionally the k-space resampling of the second subset of input data, the input data are subjected to processing involving at least one of the following steps, and preferably all of the following steps:

removing the constant components of the input data;

converting the input data from a light wavelength domain λ to input data in a wavenumber domain k, where $$k = \frac{2\prod}{\lambda},$$

especially so that the input data would be equidistant from each other as a function of the wavenumber k;

and after the k-space resampling of the first subset of input data and optionally the k-space resampling of the second subset of input data, the input data are subjected to processing involving at least one of the following steps, and preferably all of the following steps:

numerical compensation of the dispersion between the reference path 4 and the sample path 5;

conversion of the output data into a spatial domain, especially by means of the Discrete Fourier Transform, DFT, or the Fast Fourier Transform, FFT;

recalculation of the output data into colours or shades of grey of the tomogram, especially with an eight-bit grey scale.

Preferably, the first set of calibration parameters and the first subset of output data correspond to the first resolution and the first height of the imaging window. On the other hand, the second set of calibration parameters and the second subset of output data correspond to the second resolution and the second height of the imaging window.

Preferably, the first set of calibration parameters defines a strictly monotonic function within a range from $n1_{in\_min}$ to $n1_{in\_max}$, while the second set of calibration parameters defines a strictly monotonic function within a range from $n2_{in\_min}$ to $n2_{in\_max}$.

Preferably, the first set of calibration parameters is constituted by the coefficients of a first polynomial, especially with a degree of 4, while the second set of calibration parameters is constituted by the coefficients of a second polynomial, preferably with a degree of 4.

Preferably, the detector which is used comprises a line of N photosensitive elements, preferably a line of 2048 photosensitive elements, or the detector which is used comprises a photodiode.

Preferably, numerical processing of the input data uses software run on a computer, a tablet or a smartphone, or it uses a appropriately programmed system of a field-programmable gate array, or an application-specific integrated circuit.

Preferably, the object under examination is biological tissue, in particular the eye tissue.

Preferably, all of the input data, i.e. all N measurement results forming a vector with coordinates numbered from 0 to N−1, have been recorded as a result of a single measurement of the object under examination.

The purpose of the invention is also to provide a system for numerical processing of input data, comprising a processor and memory, configured and programmed to implement the method according to the above description.

Moreover, the purpose of the invention is to provide an optical coherence tomography device, OCT, comprising the system described above. In particular, the system according to the invention is a swept source optical coherence tomography or spectral domain optical coherence tomography device.

DESCRIPTION OF THE DRAWINGS

The invention will now be presented in more detail in a preferable embodiment, with reference to the attached drawings, in which.

SYMBOLS IN THE DRAWINGS

Figure 1:
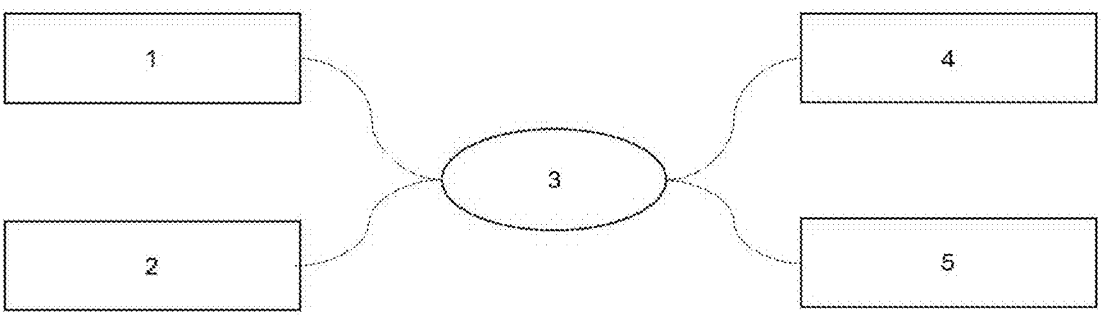
FIG. 1 Presents a simplified block diagram of an OCT device.

1—light source
2—detector
3—coupler
4—reference path
5—sample path
7—collimating lens
8—diffraction grating
9—focusing lens
10—photosensitive elements
11—output data
12—input data

DETAILED DESCRIPTION OF THE PREFERRED EMBODIMENT OF THE INVENTION

According to the invention, an OCT device (optical coherence tomography) is provided, made using one of the FD-OCT technologies (Fourier Domain Optical Coherence):

- swept source optical coherence tomography—swept source OCT (SS-OCT), using a tunable laser to generate tomographic cross-sections
- spectral-domain OCT (SD-OCT)—using a light source 1 with low temporal coherence and a spectrometer to measure the interference signal.

The OCT device according to the invention uses an interferometer system. The light emitted by the light source 1 is split in a coupler 3 into at least two paths: at least one reference path 4, in which a reference light beam is reflected from a mirror, and at least one sample path 5, in which a sample light beam is reflected from the object under examination, preferably biological tissue, and even more preferably eye tissue. After reflecting in these paths, the reference beam and the sample beam return along the same way, and they merge and interfere with each other in the coupler 3. Subsequently, the merged beam reaches a detector 2, where data are recorded in the form of a spectrum of merged light beams in a specified light wavelength range as a vector of N measurement results.

When using an SD-OCT type device, the detector 2 has the form of a spectrometer. During a single measurement of the object under examination, the device performs the following operations: the light source 1 generates light with a specified wavelength range. The wavelength range is selected so as to obtain the desired resolution and imaging window. After exiting the coupler 3, the light beams are jointly cast onto a collimating lens 7, following which a parallel beam is cast onto a diffraction grating 8. In this place, the wavelengths become separated from each other, and they are subsequently focused by means of a focusing lens 9 in the detector 2, which collects information in the form of interference fringes. In the case of an SD-OCT device, the detector 2 comprises a line of N photosensitive elements 10, on which the interference fringes are recorded in the form of a vector of N measurement results. The line according to an embodiment can be any arrangement comprising photosensitive elements, e.g. a charge-coupled device, or a complementary metal-oxide semiconductor, the line not being required to have only a single row of photosensitive elements, which means that only one row of photosensitive elements of a rectangular matrix can be used, or matrices with a single row of photosensitive elements can be used. According to an embodiment, the line of photosensitive elements 10 has 2048 elements, but it can have any number thereof, limited by commercially available matrices of photosensitive elements; preferably, N equals the consecutive powers of the number two. The information recorded in this manner in the line of N photosensitive elements 10 constitutes a set of input data 12.

In the case of an SS-OCT device, the detector 2 has the form of at least one photodiode. Due to a major difference between the structure of an SD-OCT and an SS-OCT detector, a single measurement of an object is to be understood as a process involving the performance of a series of N measurements of the object under examination, each with a different wavelength generated by the light source 1 according to the following operations. The photodiode is located at the outlet of an optical fibre, and it records the intensity of the entire light cast onto it. The light source 1 simultaneously emits light with a specified wavelength, changing the light length with each consecutive measurement, so that N consecutive measurements are performed during a single measurement of the object under examination, each for the next specified wavelength in the form of a vector of N measurement results. The wavelength range is selected to obtain the desired resolution and imaging window. According to an embodiment, 2048 measurements are performed during a single measurement, but any number thereof can be performed; preferably, N equals the consecutive powers of the number two. Additionally, in SS-OCT devices it is also possible to use at least two couplers 3, which split the beam into at least two beams, so that the signal is recorded by means of at least two photodiodes, which reduces the recorded noises.

SD-OCT and SS-OCT devices are characterised by the height of the imaging window and the height of the tomogram presented in pixels. The height of the tomogram is a constant value for a series of devices, assigned in advance. The height of the window in the case of SD-OCT directly depends in turn on the calibration parameters determined for the detector 2. A single set of calibration parameters means that the imaging window will always have the same size, that is, the image will have the same resolution. However, it is possible to determine calibration parameters for two or more heights of the imaging window, that is, in a manner which will enable obtaining a denser and sparser distribution of the fringes with respect to the fringes generated by means of a detector 2 with a set of calibration parameters known from prior art, determined in a standard manner. The generation of an image with a denser and narrower distribution of fringes is possible for a single measurement of the object under examination, which means that images with a zoomed-in or zoomed-out window do not have to be separated in time. In the case of SS-OCT devices, the collected signal is linear in a function of the wavenumber. In this case, the set of calibration parameters may be used for the k-space resampling of the input data 12, in order to achieve the same objective as in the case of SD-OCT devices—meaning to obtain any number of heights of the imaging window.

Figure 3:
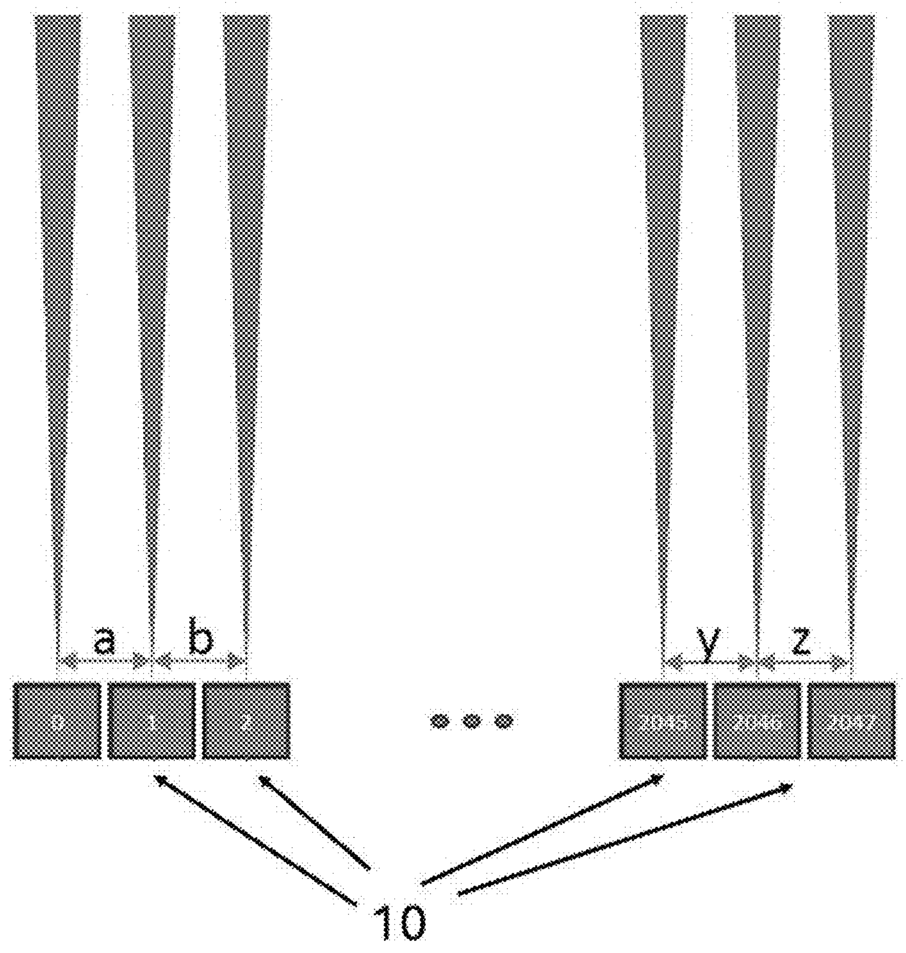
FIG. 3 Presents a line of photosensitive elements.
Figure 4:
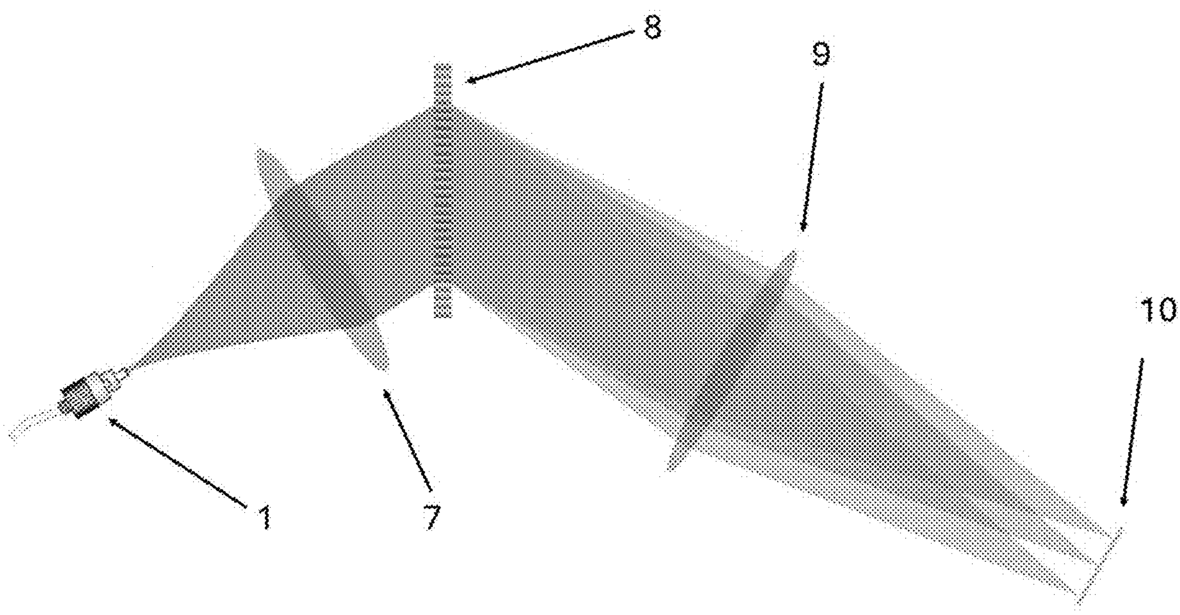
FIG. 4 Presents a detector in the form of an interferometer.
Figure 5:
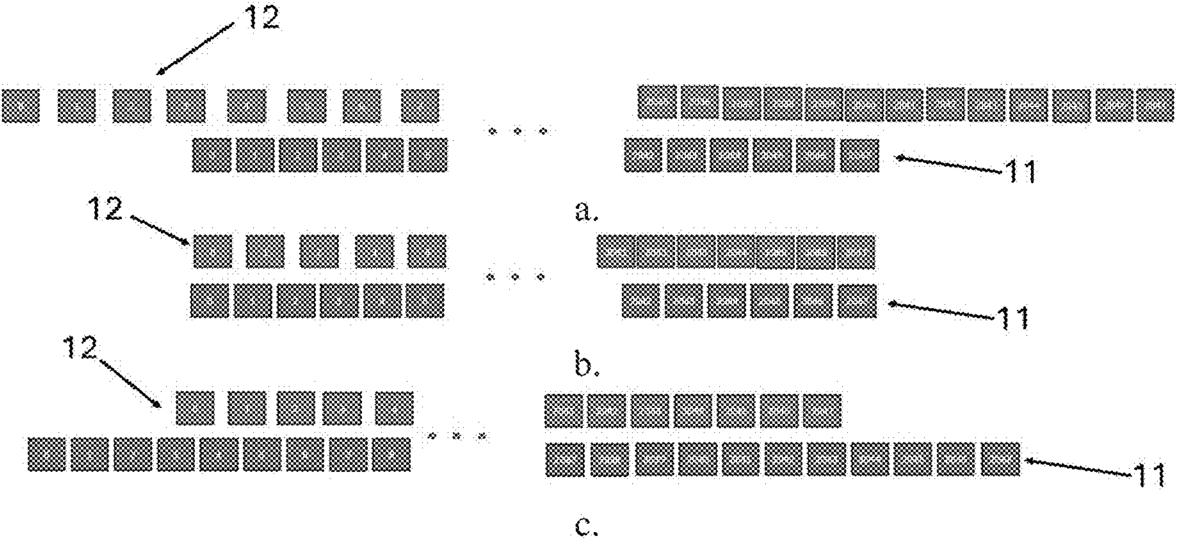
FIG. 5 Presents exemplary methods for k-space resampling input data into output data FIG. 6 Presents a graph showing the dependence of the input data on the output data after k-space resampling by means of a first set of calibration parameters.
Figure 6:
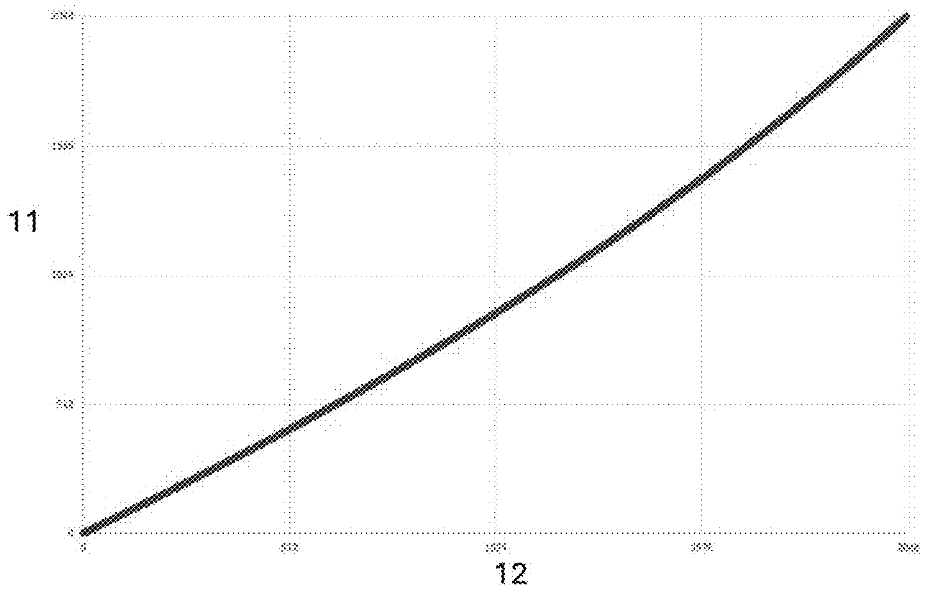
Figure 7:
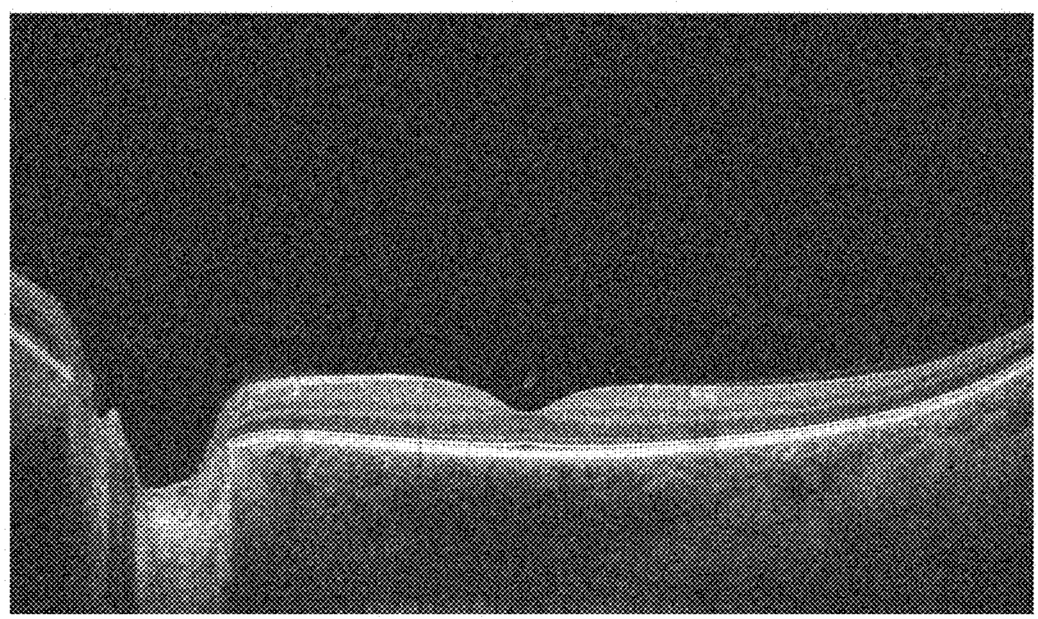
FIG. 7 Presents a tomogram generated on the basis of the data from FIG. 6

Calibration parameters are to be understood as parameters describing the manner of replacing one set of data with the other one. According to the invention, a monotonic function is used as the set of calibration parameters, and more precisely the consecutive coefficients of a polynomial, preferably a polynomial with a degree of four. A person skilled in the art could easily imagine other ways of recalculating one set of data into the other, for example by polynomial functions with a degree of N, trigonometric functions, a look-up table, formulas created using empirical methods, etc. An example of a function expressed by a set of calibration parameters is presented in FIG. 1, FIG. 3 and FIG. 5.

Figure 2:
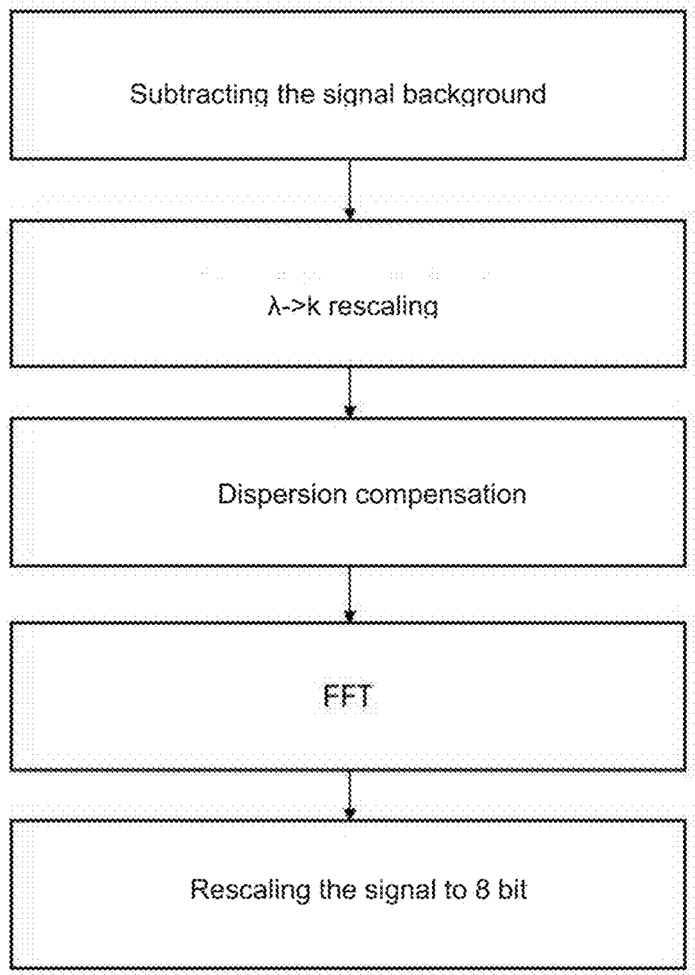
FIG. 2 Presents a block diagram of an image generation process based on input data.

According to the first embodiment, the input data 12 recorded in the OCT device in the form of a vector of N measurement results are subjected to processing comprising the following steps (FIG. 2):

a. Deleting the constant components of the input data 12.
b. Converting the input data 12 from a light wavelength domain λ into input data 12 in a wavenumber domain k, where $k=2\Pi/\lambda$. Fringes generated as a result of imaging are distributed in an uneven manner, at various distances from each other. Each device provided with a spectrometer has its specified characteristic set of calibration parameters. If the fringes were subjected to further processing (omitting the step involving the λ->k signal resampling) and displayed as an output image, this image would be blurred, due to the distribution of the fringes. For example, if an item consisting of a single layer were to be placed in the sample arm, the signal recorded in the detector 2 would present the sine function, whose frequency would be variable, meaning that, e.g. the function would be stretched on one side of the image. The calculated calibration parameters are intended to resample the distribution of the fringes, so that the consecutive samples would be equidistant as a function of the wavenumber k, meaning that the fringes would be distributed every identical number of pixels. This means that the abovementioned sine function after the k-space resampling of the distribution of the fringes would no longer be stretched, and its image would have a single frequency, just like the object.
c. K-space resampling a first subset of input data 12, i.e. the input data 12 saved in said vector of N measurement results as coordinates numbered from $n1_{in\_min}$ to $n1_{in\_max}$, where $0 \leq n1_{in\_min} < n1_{in\_max} \leq N-1$, wherein this k-space resampling is described by means of a first set of calibration parameters, into a first subset of output data 11, in which first subset of output data 11, the values of the output data 11, meaning the data after k-space resampling, are saved in the form of a first vector of output data 11, with coordinates numbered from $n1_{out\_min}$ to $n1_{out\_max}$.
d. k-space Resampling a second subset of input data 12, i.e. the input data 12 saved in said vector of N measurement results as coordinates numbered from $n2_{in\_min}$ to $n2_{in\_max}$, where $0 \leq n2_{in\_min} < n2_{in\_max} \leq N-1$, wherein this k-space resampling is described by means of a second set of calibration parameters, into a second subset of output data 11. In the second subset of output data 11, the values of the output data 11, meaning the data after k-space resampling, are saved in the form of a second vector of output data 11, with coordinates numbered from $n2_{out\_min}$ to $n2_{out\_max}$. Wherein the first subset of input data 12 differs in at least one element from the second subset of input data 12, and/or the first set of calibration parameters differs in at least one parameter from the second set of calibration parameters.
e. Compensation of the dispersion between the reference path 4 and the sample path 5
f. Conversion of the output data 11 into a spatial domain, especially by means of the Fast Fourier Transform, FFT;
g. Recalculation of the first, and preferably the first and the second output data 11, into colours or shades of grey of the tomogram, preferably with an eight-bit grey scale.

Additionally, the conversion of the input data 12 into the output data 11 depending on the data collected during a single measurement can be done in any manner, by means of various kinds of calibration parameters. For example, the first subset of input data 12 may be resampled into the first subset of output data 11 by means of first calibration parameters described by means of a trigonometric function, and subsequently, at the user's request, the second and consecutive k-space resamplings are done by means of calibration parameters described by means of a polynomial with a degree of two.

Numerical processing of the input data 12 uses software run on an OCT device, on an external device or in a cloud, preferably provided with non-volatile or volatile memory. The calculations can use any device capable of performing calculations, for example: a computer, a telephone, a tablet, a properly programmed system of a field programmable gate array (FPGA), or an application-specific integrated circuit (ASIC).

It should be noted that there are numerous possible variations which do not limit the operating principle of the solution in question. The only necessary steps are steps c and d, and all the remaining steps constitute methods known from prior art, used to generate a final image and improve its quality.

For example, according to a second embodiment, step a. is omitted, thus saving processing power at the expense of image quality.

According to another embodiment, the input data 12 are converted from a light wavelength domain into input data 12 in a wavenumber domain directly by a function described by the first set of calibration parameters and the second set of calibration parameters, combining step b with steps c and/or d.

According to yet another embodiment, after steps c and d, any amount of further output data 11 can be generated analogically at the user's request, by k-space resampling the consecutive subsets of input data 12 into the consecutive subsets of output data 11 by means of further calibration parameters, not necessarily the same type of calibration parameters.

The resolution and height of the imaging window of a tomogram generated on the basis of the output data 11 depend on the selected subset of input data 12 and the calibration parameters.

The user may choose the resolution and height of the imaging window at will, depending on the needs.

If the user performs k-space resampling while only ensuring even distribution of the fringes along the entire imaging window, the result is an image known from prior art, meaning one with the highest resolution, with the specified imaging window, using the entire range of the input data 12. This example is presented in FIG. 5*b*, for a vector with indices from 0 to N−1, where N=2048. In this case, the output data 11 resampled by means of the calibration parameters has a similar spectral width as the input data 12. It should also be noted that the labelling of indices from 0 to N−1 should not be considered limiting; this labelling is indeed arbitrary, and it can be labelled with a different interval of integers.

Figure 8:
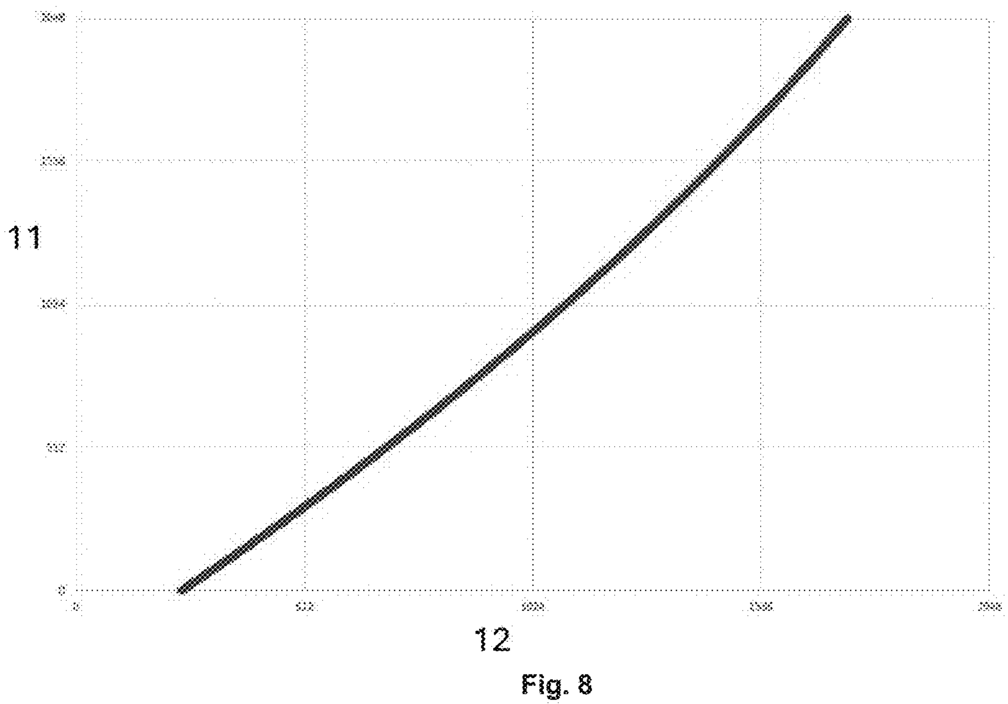
FIG. 8 Presents a graph showing the dependence of the input data on the output data after k-space resampling by means of a second set of calibration parameters.

An imaging window generated with the use of a set of calibration parameters ensuring denser distribution of fringes will be lower than the standard imaging window. This example is presented in FIG. 5*c*, for a vector with indices from 0 to N−1, where N=2048. In this case, the output data 11 resampled by means of the calibration parameters has a greater spectral width than the input data 12. This means that the spectral range does not change; it is simply rescaled by means of numerical methods. The output image, which will be generated as a result of further processing of the resulting data, will present a structure extended towards the z axis, since this image will be "stretched" to the size of the standard imaging window. Therefore, the imaged structure will have a higher resolution, as shown in FIG. 8 and FIG. 9.

Figure 9:
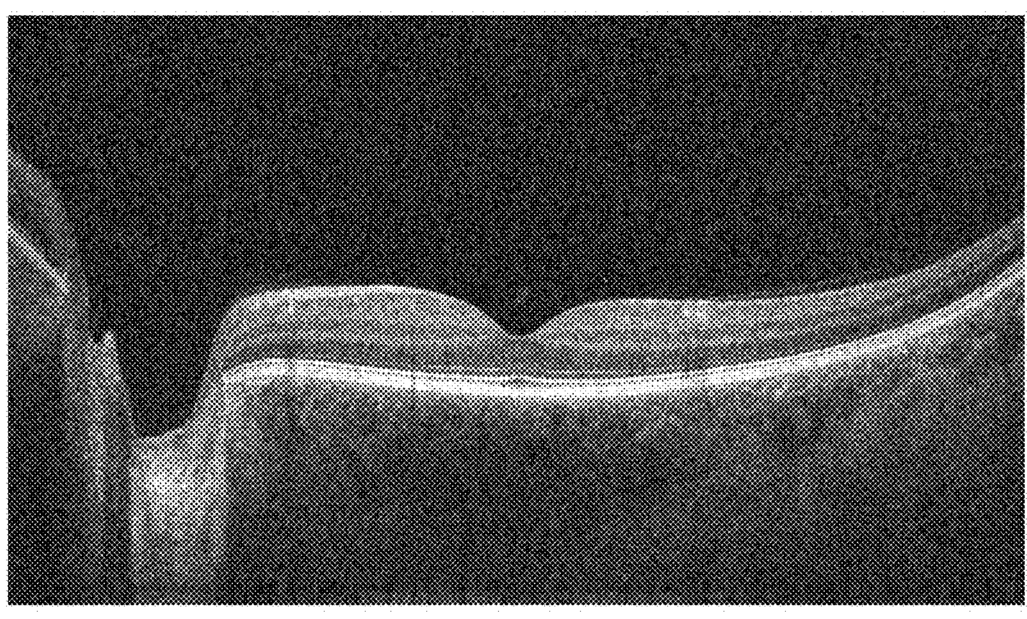
FIG. 9 Presents a tomogram generated on the basis of the data from FIG. 8
Figure 10:
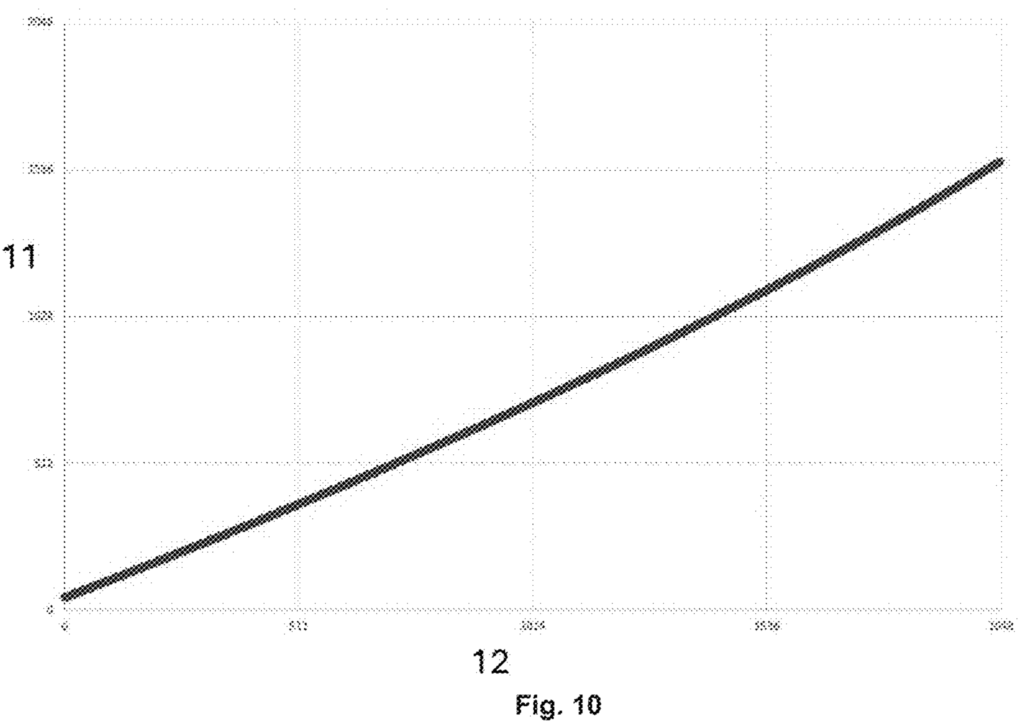
FIG. 10 Presents a graph showing the dependence of the input data on the output data after k-space resampling by means of a third set of calibration parameters.
Figure 11:
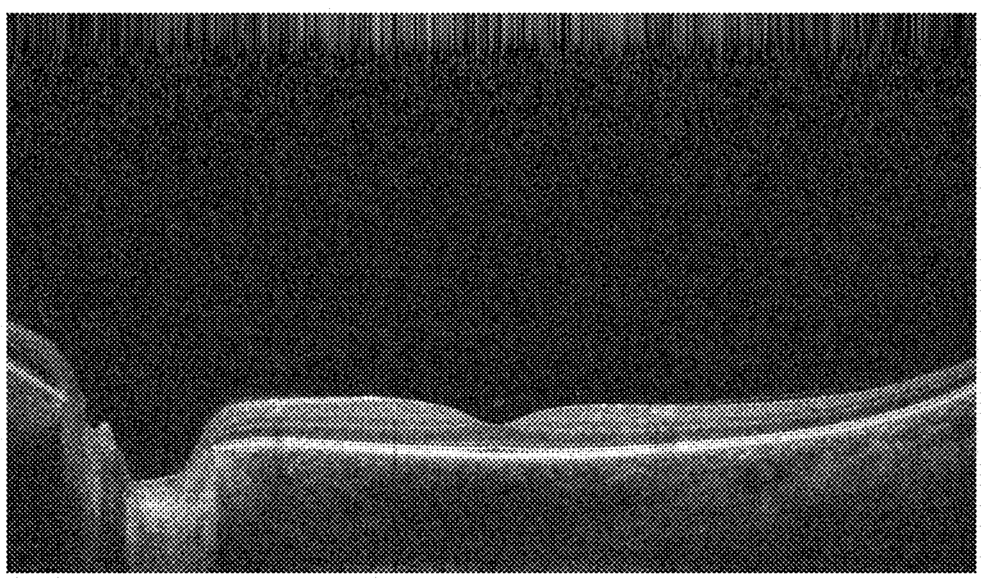
FIG. 11 Presents a tomogram generated on the basis of the data from FIG. 10

According to an embodiment, the images presented in FIG. 9 were generated using the k-space resampling of a subset of input data 12 into output data 11 by means of the following calibration parameters:

$x_0$=−238.94, $x_1$=0.97, $x_2$=1.69 E−0.04, $x_3$=−5.1 E−0.08, $x_4$=4.04 E−11, describing the following function $(((px_4+x_3)*p+x_2)*p+x_1)*p+x_0$ For an imaging window generated with the use of a set of calibration parameters ensuring a sparser distribution of fringes, the window will in turn be higher than the standard imaging window. This example is presented in FIG. 5*a*, for a vector with indices from 0 to N−1, where N=2048. In this case, the output data 11 resampled by means of the calibration parameters has a narrower spectral width than the input data 12. The output image which will be generated as a result of further processing will present a structure shrunk towards the z axis, since this image will be "compressed" to the size of an imaging window for the standard parameters. This will cause a drop in resolution, but a greater depth range will be imaged instead, which means that more structures will be visible towards the z axis, as shown in FIG. 10 and FIG. 11. According to an embodiment, the images presented in FIG. 11 were generated using the k-space resampling of a subset of input data 12 into output data 11 by means of the following calibration parameters:

$x_0$=42.7, $x_1$=0.61, $x_2$=4.84−0.05, $x_3$=−1.21 E−0.09, $x_4$=4.47 E−12, describing the following function $(((px_4+x_3)*p+x_2)*p+x_1)*p+x_0$ Such diversification will allow for zooming in to or zooming out from the structures under examination, depending on the parameters specified by the user. This method can be found particularly applicable when imaging the pathological structures of the eye. Zooming freely in will allow for more precise diagnostics of small pathological changes which take place in the eye, due to the higher resolution and a larger size of the pathological change in the image. On the other hand, zooming out will allow for imaging large pathological changes, which reach beyond the imaging window for the standard size of the imaging window. This way, observation of these changes is possible with no need to perform repeated measurements. On the basis of a single measurement of the eye, the user is able to freely zoom in to or zoom out from the structure under examination.

One should also notice other advantages of this solution, especially compared to devices, in which a change in the imaging window is achieved by means of changes in the optical system of the device.

- In the software solution, a change in the size of the imaging window does not require changes in the optical system.
- In such a device, there are less moving elements that could malfunction.
- It does not require the device to have additional optical and mechanical elements either, which is why it is cheaper to produce.
- It does not require a larger number of calculations, but only the use of other calibration parameters.
- When errors related to a change in the imaging window occur, updates of the software or the FPGA configuration can be performed remotely.

The invention claimed is:

1. A computer-implemented method for numerical processing of input data, which input data have the form of N measurement results forming a vector with coordinates numbered from 0 to N-1, and which input data have been registered in a detector, in an optical coherence tomography device, OCT, during a process involving:

- the emission of light by a light source,
- splitting the light in a coupler into at least two paths, meaning:
  - at least one reference path, in which a reference light beam is reflected from a mirror,
  - at least one sample path, in which a sample light beam is reflected from the object under examination,
- reflecting said reference light beam in at least one reference path from the mirror, and
- reflecting said sample light beam in at least one sample path from the object under examination,
- merging and interference of the reference light beam and the sample light beam in the coupler,
- optional passing of the merged light beams across a diffraction grating,
- recording the data in the form of a spectrum of merged light beams within a specified light wavelength range by means of said detector as said vector of N measurement results, k-space resampling a first subset of input data, i.e. the input data saved in said vector of N measurement results, as coordinates numbered from $n1_{in\_min}$ to $n1_{in\_max}$, where $0 \leq n1_{in\_min} < n1_{in\_max} \leq N-1$, which k-space resampling is described by means of a first set of calibration parameters, into a first subset of output data, in which first subset of output data, the values of the output data, meaning the data after resampling, are saved in the form of a first vector of output data, with coordinates numbered from $n1_{out\_min}$ to $n1_{out\_max}$, characterised in that it comprises the step of at the user's request, resampling a second subset of input data, i.e. the input data saved in said vector of N measurement results as coordinates numbered from $n2_{in\_min}$ to $n2_{in\_max}$, where $0 \leq n2_{in\_min} < n2_{in\_max} \leq N-1$, which resampling is described by means of a second set of calibration parameters, into a second subset of output data, in which second subset of output data the values of the output data, meaning the data after k-space resampling, are saved in the form of a second vector of output data, with coordinates numbered from $n2_{out\_min}$ to $n2_{out\_max}$, the first subset of input data being different in at least one element from the second subset of input data, and/or the first set of calibration parameters being different in at least one parameter from the second set of calibration parameters, wherein the first output data resampled by means of the first calibration parameters has a greater or narrower spectral width of wavelength in comparison to the second output data resampled by means of the second calibration parameters.

2. The method according to claim 1, characterised in that a first tomogram with a first resolution and a first height of the imaging window is generated on the basis of the first subset of output data, and moreover, at the user's request, a second tomogram with a second resolution and a second height of the imaging window is generated on the basis of the second subset of output data.

3. The method according to claim 2, characterised in that the first resolution is different from the second resolution, and/or the first height of the imaging window is different from the second height of the imaging window.

4. The method according to claim 1, characterised in that prior to the k-space resampling of the first subset of input data and optionally the k-space resampling of the second subset of input data, the input data are subjected to processing involving at least one of the following steps, and preferably all of the following steps:

removing the constant components of the input data, converting the input data from a light wavelength domain λ to input data in a wavenumber domain k, where $$k = \frac{2\Pi}{\lambda},$$

especially so that the input data would be equidistant from each other as a function of the wavenumber k;

while after the k-space resampling of the first subset of input data and optionally the k-space resampling of the second subset of input data, the input data are subjected to processing involving at least one of the following steps, and preferably all of the following steps:

numerical compensation of the dispersion between the reference path and the sample path;

conversion of the output data into a spatial domain, especially by means of the Discrete Fourier Transform, DFT, or the Fast Fourier Transform, FFT;

recalculation of the output data into colours or shades of grey of the tomogram, especially with an eight-bit grey scale.

5. The method according to claim 1, characterised in that the first set of calibration parameters and the first subset of output data correspond to the first resolution and the first height of the imaging window, while the second set of calibration parameters and the second subset of output data correspond to the second resolution and the second height of the imaging window.

6. The method according to claim 1, characterised in that the first set of calibration parameters defines a strictly monotonic function within a range from $n1_{in\_min}$ to $n1_{in\_max}$, while the second set of calibration parameters defines a strictly monotonic function within a range from $n2_{in\_min}$ to $n2_{in\_max}$.

7. The method according to claim 1, characterised in that the first set of calibration parameters is constituted by the coefficients of a first polynomial, especially with a degree of 4, while the second set of calibration parameters is constituted by the coefficients of a second polynomial, especially with a degree of 4.

8. The method according to claim 1, characterised in that the detector which is used comprises a line of N photosensitive elements, preferably a line of 2048 photosensitive elements, or the detector which is used comprises a photodiode.

9. The method according to claim 1, characterised in that numerical processing of the input data uses software run on a computer, a tablet or a smartphone, or it uses a properly programmed system of a field-programmable gate array, or an application-specific integrated circuit.

10. The method according to claim 1, characterised in that the object under examination is biological tissue, in particular eye tissue.

11. The method according to claim 1, characterised in that all of the input data, i.e. all N measurement results forming a vector with coordinates numbered from 0 to N−1, have been recorded as a result of a single measurement of the object under examination.

12. A system for numerical processing of input data, comprising a processor and memory, configured and programmed to implement the method according to claim 1.

13. An optical coherence tomography device, OCT, comprising the system according to claim 12, especially constituting a swept source optical coherence tomography or spectral domain optical coherence tomography device.

* * * * *